(12) United States Patent
Delahanty et al.

(10) Patent No.: US 12,217,860 B2
(45) Date of Patent: Feb. 4, 2025

(54) MEDICAL IMPLANT SOFTWARE SYSTEMS AND METHODS

(71) Applicant: CraniUS LLC, Baltimore, MD (US)

(72) Inventors: Conner Delahanty, Baltimore, MD (US); Aayush Gandhi, Baltimore, MD (US); Rahul Gangwani, Baltimore, MD (US); Maximilian Zinkus, Baltimore, MD (US); Simone Bliss, Baltimore, MD (US); Tiger Gao, Baltimore, MD (US); Owen Friesen, Baltimore, MD (US); John Cai, Baltimore, MD (US); Vivian Looi, Baltimore, MD (US); Isaac Lefkovitz, Baltimore, MD (US)

(73) Assignee: CraniUS LLC, Baltimore, MD (US)

( * ) Notice: Subject to any disclaimer, the term of this patent is extended or adjusted under 35 U.S.C. 154(b) by 0 days.

(21) Appl. No.: 18/442,614

(22) Filed: Feb. 15, 2024

(65) Prior Publication Data

US 2024/0249833 A1 Jul. 25, 2024

Related U.S. Application Data

(63) Continuation of application No. 18/306,474, filed on Apr. 25, 2023, now Pat. No. 11,937,089.
(Continued)

(51) Int. Cl.
*H04W 12/50* (2021.01)
*G16H 40/40* (2018.01)
(Continued)

(52) U.S. Cl.
CPC ............. *G16H 40/40* (2018.01); *G16H 40/67* (2018.01); *G16H 80/00* (2018.01); *H04W 12/037* (2021.01); *H04W 12/50* (2021.01)

(58) Field of Classification Search
CPC ..... H04W 12/50; H04W 12/037; G16H 40/67
See application file for complete search history.

(56) References Cited

U.S. PATENT DOCUMENTS 9,980,140 B1 * 5/2018 Spencer ................. H04W 12/02
10,661,010 B1 * 5/2020 Tsinberg ............ A61M 5/14276
(Continued)

OTHER PUBLICATIONS

Search Report and Written Opinion issued on Sep. 21, 2023, in corresponding International Application No. PCT/US 23/66481, 8 pages.

*Primary Examiner* — Khalid M Almaghayreh
(74) *Attorney, Agent, or Firm* — Maier & Maier, PLLC (57) ABSTRACT

A method for remotely bonding a companion device to an implanted medical device to achieve long-term encrypted and authenticated communication channel, that is resilient to companion device failure or compromise and hence mitigates the risk or need for unplanned, revision surgery and/or premature device explantation. Through use of a shared cryptographic key between the two systems, the companion device may request an encrypted challenge number from the implant. Completing the challenge via transmitting an encrypted validation number permits the implanted medical device to bond and perform a new long-term key exchange. The shared cryptographic key can be changed as well, in event of compromise or other adverse event, using a described device firmware update procedure.

10 Claims, 4 Drawing Sheets

Related U.S. Application Data (60) Provisional application No. 63/355,262, filed on Jun. 24, 2022.

(51) Int. Cl.
*G16H 40/67* (2018.01)
*G16H 80/00* (2018.01)
*H04W 12/037* (2021.01)

(56) References Cited

U.S. PATENT DOCUMENTS

| | | | |
|---|---|---|---|
| 2008/0249591 A1* | 10/2008 | Gaw | A61N 1/37235 607/60 |
| 2010/0114251 A1 | 5/2010 | Behm | |
| 2010/0292556 A1* | 11/2010 | Golden | G16H 40/40 607/31 |
| 2012/0271380 A1* | 10/2012 | Roberts | H04L 63/068 607/60 |
| 2014/0273824 A1* | 9/2014 | Fenner | H04B 5/79 455/41.1 |
| 2015/0087934 A1* | 3/2015 | Pless | A61B 5/021 600/302 |
| 2017/0161449 A1* | 6/2017 | Meskens | G16H 40/40 |
| 2017/0257761 A1* | 9/2017 | Rodriguez | H04L 67/12 |
| 2018/0043168 A1* | 2/2018 | Kim | H04W 12/50 |
| 2018/0084106 A1* | 3/2018 | Li | G06F 3/017 |
| 2018/0109946 A1* | 4/2018 | Mosenia | H04W 12/06 |
| 2018/0241564 A1* | 8/2018 | Peterson | A61N 1/37254 |
| 2018/0243573 A1* | 8/2018 | Yoder | H04L 63/18 |
| 2018/0289969 A1* | 10/2018 | Malekkhosravi | A61N 1/37223 |
| 2019/0015669 A1* | 1/2019 | Muessig | A61B 5/0028 |
| 2020/0094062 A1 | 3/2020 | Yoder et al. | |
| 2020/0367055 A1* | 11/2020 | Caruso | G16B 40/67 |
| 2021/0377726 A1* | 12/2021 | Finney | H04W 12/71 |
| 2021/0377740 A1* | 12/2021 | Prutchi | A61N 1/37254 |
| 2022/0047378 A1 | 2/2022 | Gordon | |
| 2022/0159468 A1* | 5/2022 | Prutchi | H04B 5/79 |
| 2023/0355995 A1* | 11/2023 | Forsell | H04W 76/10 |

* cited by examiner

MEDICAL IMPLANT SOFTWARE SYSTEMS AND METHODS

CROSS-REFERENCE TO RELATED APPLICATIONS

This application is a continuation of U.S. application Ser. No. 18/306,474, filed August Apr. 25, 2023, and claims priority and the benefit of U.S. Provisional No. 63/355,262, Filed Jun. 24, 2022, the entire contents of each of which are hereby incorporated by reference.

BACKGROUND

The use of drug delivery implants has reduced required and/or repetitive surgeries, targeted specific areas of the body, thereby increasing drug safety and efficacy, and eased the process of providing lifesaving medicine; such as when, for example, surgery is deemed suboptimal and/or less effective, like with chronic disease management and/or when systemic/oral medicine dosing is ineffective in crossing a homeostatic cellular barrier (i.e. blood brain barrier) and reaching the target organ or tissue. However existing medical implants are limited in their ability to monitor and control the implants' various components by a number of factors. Furthermore, existing medical implants in use today—which are controlled wirelessly without any transcutaneous wiring (i.e. NeuroPace for brain epilepsy, cardiac pacemakers for abnormal heartbeats, etc), must all be controlled from a very close distance (i.e. within several inches) via a close proximity transducer placed directly above one's scalp/skin.

First, medical implants have a heightened need for security and robustness of firmware or software, as if a bug were to occur or an unauthorized person were to gain access to the medical implant there could be disastrous or even lethal consequences to the patient. Second, there is a need to reduce or eliminate the need to physically access the medical implant for updating, controlling, or restoring compromised components (i.e., change in function regarding pump-assisted catheter flow, alter dosage administration via a medicine pump, etc), as physically accessing the device may require the patient to undergo a risky, costly and potentially dangerous surgery. For example, it is well known that for each skin-opening procedure near a medical implant, the risk of infection drastically increases exponentially. In addition, this inability to achieve smart, wireless, connectivity increases the overall time it may take to see and respond to urgent/emergent medical issues, such as the potential for overdosing/underdosing in instances of an acute change in one's medical status. For example, if a skull-embedded medicine pump was in the daily process of treating a malignant brain tumor via convection-enhanced delivery, but the patient's brain swelling increased suddenly due to underlying disease progression and intracranial hypertension ensued, then the implanted device would need to have the medicine flow emergently stopped to prevent life-threatening herniation. However, in the current state-of-the-art, implanted medical devices need to be in very close proximity to the treating physician so that the transducer can be just a few inches away from the scalp/skin—and thus, for this scenario, the patient would most likely die in the interim.

Third, there is a need to be able to remotely view data, to allow healthcare providers and patients to adjust to changing situations and better facilitate patient care. For instance, if a patient had a skull-embedded medicine delivery device treating an underlying brain tumor, and a recent imaging exam (i.e. MRI showed unexpected resolution of disease with a complete response), then the doctor/surgeon may want to stop and/or reduce the daily chemotherapy treatment almost immediately given the change in his/her oncological status; with the obvious reason being that there is no justification to deliver continuous, toxic brain tumor medicine if and when one's brain tumor has shrunken and/or gone into remission. However, if the patient were to live in a different state or country from the treating physician/surgeon, then this type of important adjustment could be impossible for several days, weeks or months—depending on access to national or international travel (i.e., time factor, financial implications, family-social obstacles, etc). Thus, unfortunately, many existing devices are not able to sufficiently address these challenges, and therefore must greatly limit their reliance on software or firmware, which decreases the potential effectiveness of the device.

Additionally, there is an increasing trend of government regulations that strictly govern cybersecurity of medical devices, and thus many existing devices do not have the cybersecurity framework necessary to continue operating under these new guidelines.

SUMMARY

In some embodiments, a method for remotely bonding a companion device to an implanted medical device may be provided. The method may include, when no device is bonded to the implanted medical device, advertising a periodic bonding signal containing an encrypted number from the implanted medical device. The cryptographic key associated with the implanted medical device may then be provided to the companion device and the periodic bonding signal from the implanted medical device may be received. The encrypted number transmitted by the periodic bonding signal data may then be decrypted using the cryptographic key information, which may result in a decrypted number and a response to the decrypted number may be created. The companion device may encrypt the response to the decrypted number. The encrypted response to the decrypted number may be transmitted to the implanted medical device. The implanted medical device may then validate the transmitted response and establish a bonded connection between the companion device and the implanted medical device.

In some embodiments a system for remotely bonding a companion device to an implanted medical device may be provided. The system may include an implanted medical device that periodically determines if a companion device is bonded to the implanted medical device. It may be determined no device is bonded to the implanted medical device if a return handshake is not detected after a predetermined amount of time. If no device is bonded to the implanted medical device, then the implanted medical device may periodically advertise a signal containing an encrypted number that is encrypted by a cryptographic key associated with the implanted medical device.

The system may further include a companion device which may be provided with the cryptographic key associated with the implanted medical device and which may receive the periodic bonding signal from the implanted medical device, determine a decrypted number by decrypting the encrypted number using the cryptographic key information, create a response to the decrypted number, encrypt the response to the decrypted number, and transmit the encrypted response to the decrypted number to the implanted medical device.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

In one or more exemplary embodiment a medical implant device may be provided. The medical implant may be, for example but not limited to, a cranial medical implant, a knee implant, a spinal implant, etc. The medical implant may perform the function of, for example but not limited to, delivering medication, monitoring conditions of the body, detecting medical emergencies with life-threatening consequences, etc.

In an exemplary embodiment firmware may be implemented on a processor or microcontroller, which may control the medical implant device. The medical implant device and related firmware may be able to support various forms of communication, including for example low energy Bluetooth (BLE) wireless communication, Wi-Fi communication, device firmware over the air update (DFU OTA) functionality, or any other communication methodology known in the art. The firmware may support a variety of functionalities, including but not limited to; controlling wireless connections and communication; reading medical implant sensors; controlling the medical implant to dispense medication through, for example, pumps; data storage and encryption; and/or safety and status reporting.

In an exemplary embodiment systems and methods to securely retrieve and store data on the medical implant may be provided. The firmware may be contained in one or more sub systems, for example but not limited to, a communication control sub-system (CCS), a sensors control sub-system (SCS), a pump control sub-system (PCS), a data storage sub-system (DSS), and/or a safety and status sub-system (SSS). Each sub-system may perform a specific action and/or collect data related to a specific action or system, and may communicate through a message passing system (MPS).

Figure 1:
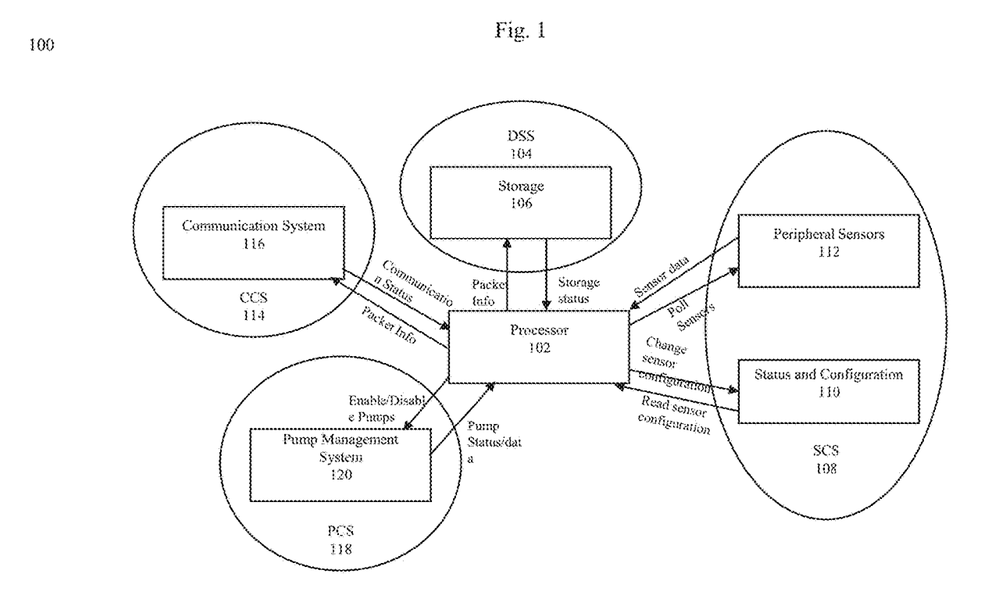
FIG. 1 is an illustration of sub-systems of an exemplary medical implant control system.

Referring now to FIG. 1, one or more exemplary sub-systems of an exemplary medical implant control system 100 may be described. The exemplary control system 100 may include a processor 102. The exemplary control system may include the DSS 104 which may contain one or more storage elements 106, such as, for example, an electronically erasable programmable read only memory (EEPROM) non-volatile storage. a ferroelectric RAM (FRAM), a flash storage device, a trusted platform module (TPM) etc. The processor 102 may send packet information to and may receive storage information from the one or more storage elements 106. The control system 100 may further include the SCS 108. The SCS 108 may include status and configuration information 110 such as, for example but not limited to, sensor configuration and sensor state, the processor 102 may enable reading of the status and configuration information 110 and may receive, for example, sensor resolution and reading frequency information from the status information 110. The SCS 108 may further include one or more peripheral sensors 112, which may include, but are not limited to, accelerometer sensors (i.e. detecting local trauma), pressure sensors (i.e. detecting a need to immediately lower a fluid pump delivery rate), temperature sensors (i.e. excessive heat may put the implanted drug-delivery device and medicinal reservoir at risk of toxic byproduct degradation), fluid level sensors (i.e. detecting a need to return to doctor's office for fill-up of an implanted, skull-embedded, brain medicine delivery device), voltage levels (i.e. detecting a need to wirelessly charge his/her implanted medical implant), received signal strength indicators (RSSI) (i.e. patient going into an environment with degraded wireless connectivity) etc. The processor may send requests to poll the sensors 112 and may receive sensor data.

The control system 100 may further include the CCS 114, which may control communication systems 116, which may be, for example, BLE, Wi-Fi, LoRaWAN, or any other communication protocol. The processor 102 may receive communication status from and may send packet information to the communication system 116. The control system 100 may further contain the PCS 118, which may include a pump management system 120. The pump management system 120 may send pump status and pump data to the processor 102 and may receive enable or disable commands. It may be understood that in different embodiments not all of the subsystems described may be utilized, or additional subsystems may be utilized in addition to those described above.

One or more of the exemplary subsystems may now be explained in more detail.

The CCS may be responsible for overall connection and communication between the plurality of sub-systems and/or between the medical implant and one or more of a companion device, which may be for example a tablet, iPad, or other mobile device, a base station, or another computing element. The CCS functions may include, for example but not limited to, controlling the intervals at which to turn communication on and off, sending packets of data based on priority if a connection to multiple devices is established, receiving and processing commands from other devices, sending angle of arrival (AoA) to another device such as the base station through the advertising interval, handling multiple intervals of communication to multiple other devices such as the companion device and/or base station, and/or securing the wireless connection, such as when bonding with another device such as the companion device.

In an exemplary embodiment the CCS may determine when to turn on communication capabilities, for example when to turn on BLE, and connect with other devices, for example the companion device or the base station. In an exemplary embodiment the CCS firmware may not actively advertise a communication signal except during a specified transmission window, creating connection cycles of on and off behavior, which may aid in preserving battery life. The CCS may continue advertising during the specified transmission window until a connection is established and/or until a specified amount of time has passed. In some embodiments the specified time for the transmission window may be adjustable by external commands.

In an exemplary embodiment the CCS may be responsible for sending packets of data, which may be received from, for example the MPS. The packets of data may include, but are not limited to, sensor data, medication dispensing data, and/or safety and status data. The CCS may receive the packets of data as encrypted packets, and may send the encrypted packets to another device, for example the companion device. If a connection to the companion device is established, the packets of data may be sent to the companion device, and the DSS or other storage may additionally be queried for any earlier-stored packets or logging information that also need to be sent. In some embodiments if the connection to the companion device fails, or the communication advertising window closes, the data packets may instead be passed to the DSS or another storage element. Any communication marked for delivery that is not successfully sent may be attempted to be sent during the next connection cycle. In some embodiments if communication fails to send multiple times the advertising window may be progressively increased each cycle until the communication is successfully received.

In some embodiments the CCS may also transmit emergency packets, which may be packets that are created in response to safety and/or security errors that are detected on or by the device. When a safety or security error occurs the CCS may bypass the normal transmission procedure and may immediately connect to the companion device and transmit the emergency packets. If the CCS cannot connect to the companion device, the CCS may modify the priority of stored data and modify the transmission window frequency and timeframe, for example the CCS may attempt to re-transmit the information every minute or every five minutes.

In some embodiments the CCS may also be responsible for processing commands from the companion device. When the command is read the CCS may forward the command to another sub-system, for example the MPS.

Figure 2:
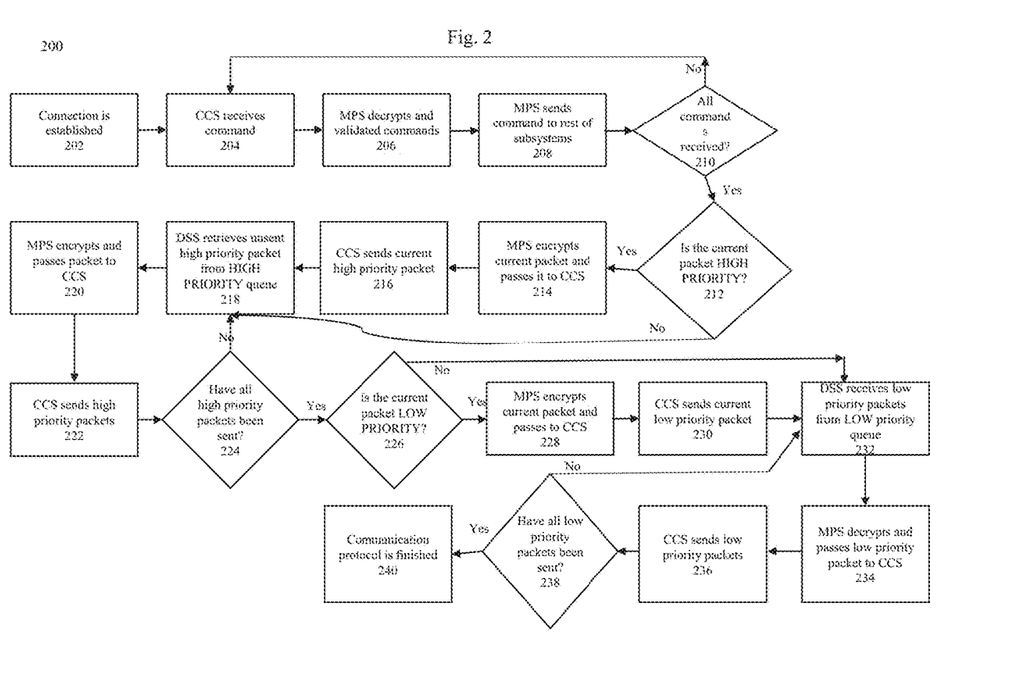
FIG. 2 is an exemplary prioritization communication flowchart.

In some embodiments the CCS may handle assigning priority for sending or receiving of data packets. Referring now to FIG. 2. an exemplary prioritization communication flowchart 200 may be shown and discussed. In a first step 202 a connection may be established between the CCS and the companion device, the connection may be, for example, a BLE connection. In a next step 204 the CCS may receive a command from the companion device. In a next step 206 the MPS may decrypt and validate the command. In a next step 208 the MPS may send the command to one or more of the other subsystems as relevant. In a next step 210 the CCS may check whether all commands have been received, if more commands are waiting then the CCS may return to 204, if all commands have been received then in a next step 212 the current packet may be assigned as high priority or low priority. If the current packet is not high priority the system may skip to step 218, if the current packet is high priority then in a next step 214 the MPS may encrypt the current packet and pass it to the CCS, and in a next step 216 the CCS may send the current high priority packet to the companion device. In a next step 218 the DSS may retrieve unsent high priority packets from the high priority queue. In a next step 220 the MPS may encrypt and pass the packets received from the DSS to the CCS. In a next step 222 the CCS may send the high priority packets. In a next step 224 the system may verify if all high priority packets have been sent, if not then the system may return to step 218, if all high priority packets have been sent then in a next step 226 it may be determined whether the current packet is low priority. If the current packet is not low priority then the system may skip to step 232, if the current packet is low priority then in a next step 228 the MPS may encrypt the current packet and pass it to the CCS. In a next step 230 the CCS may send the current low priority packet to the companion device. In a next step 232 the DSS may receive low priority packets from the LOW priority queue. In a next step 234 the MPS may decrypt and pass the low priority packets to the CCS. In a next step 236 the CCS may send the low priority packets. In a next step 238 the system may determine whether all low priority packets have been sent, if not then the system may return to step 232, if all low priority packets have been sent then the communication protocol may be finished in step 240.

In some embodiments the CCS may use multiple advertising sets to communicate with multiple devices. For example, a first advertising set may be used to communicate with the companion device and a second advertising set may be used to communicate with the base station. In other embodiments more than two advertising sets may be used to communicate with more than two other devices. In some embodiments two or more advertising sets may be advertised simultaneously.

In an exemplary embodiment the CCS may have bonding capabilities with one or more external devices. In an exemplary embodiment when the medical implant is first powered it may advertise a bonding service periodically, for example every 15 minutes or every hour. The bonding service may contain an encrypted number. The companion device may be programmed to listen for the advertising request from a specific implant and may bond with that implant in either a clinical or manufacturing setting. The companion device may read the value from the bonding characteristic, decrypt the encrypted number, and/or encrypt a validation number in its response. When the implant sends a correct validating response, the implant may bond or pair to the tablet. Once bonded the implant may switch to its normal advertising interval as discussed above. If the companion device fails to bond to the implant, or the connection is otherwise compromised, the bonding process may be repeated in a connection cycle, which may allow for re-bonding. Failure to pair may be reported to another sub-system such as the SSS, and may be reported as, for example, a security incident.

In an exemplary embodiment the SCS may be responsible for, for example, configuring and reading data from sensors and/or passing on sensor or anomaly data. In some embodiments sensor data may be stored in a data structure of pre-allocated maximum size. When data is ready for transmission, the data may be sent to the MPS to be appended to a packet structure, and then either transferred to the CCS for transmission or stored in the DSS if there is no connection. The SCS may be configured to read sensors on a certain frequency, which may be any time, for example every second, every minute, or every 15 minutes. The frequency at which the sensors are read may also be dynamic or adjusted based on commands. In some embodiments the SCS may have a separate set of logic to control the interval of RSSI readings depending on the mode the implant is set to, for example a first set of logic may be used for a tracking mode while a second set of logic is used for a charging mode.

In an exemplary embodiment the PCS may be responsible for, for example, controlling one or more medication dispensing mechanisms within the medical implant. The PCS may ensure that the medication dispensing cycles are controlled in accordance with a desired distribution or flow rate, considering other implant and distribution system parameters. The PCS may also send data related to the medication dispensing system for inclusion in any external communication, for example to the paired companion device. The medication dispensing system data may be sent to the MPS to be packaged into a packet structure, and then either transferred to the CCS for transmission or stored in the DSS if there is no connection.

In an exemplary embodiment the DSS may be responsible for, for example, dealing with long-term storage and retrieval of important device data, such as logs, packets, and the current status of the software, firmware, or hardware systems. The DSS may read and write logs and packets and may be capable of doing bulk returns on these values. In some embodiments some or all of the DSS data may be encrypted. In some embodiments the DSS may use an erasable programmable read-only memory chip (EEPROM) to read and write data, and the data stored in the DSS may be split according to different criteria or categories, for example metadata, application state, emergency packets, low priority packets, low priority logs, etc. In an exemplary embodiment any failures related to storing or retrieving information in the DSS may be reported as a safety issue, and any issues with encryption and decryption may be reported as a security issue.

In an exemplary embodiment, if a critical battery threshold is reached, the DSS may store the application state of the implant and all sub-systems, and then disable some or all of the sub-systems, for example the SCS battery and RSSI measurement systems may be left enabled while all other sub-systems are disabled. Any data may be transferred to the DSS for storage and external communication may be disabled. When a restore threshold is reached, the SSS may trigger the restoration of the state saved by the DSS, and all sub-systems may resume operation. In some embodiments some sub-systems may be restored in a disabled state and require re-enablement, for example the PCS may be restored in a disabled state and require re-enablement from the CCS. The critical battery threshold and restore threshold may be updated over time to, for example, account for performance degradation of the battery, and may be updated based on, for example, a known battery consumption model used by the companion device and/or base station.

In an exemplary embodiment the SSS may be responsible for the safe operation of the implantable medical device, for flagging or recording abnormal behavior, handling status information, and interpreting sensor values. Flagging and/or recording abnormal behavior may include, but is not limited to, detecting abnormalities, creating alerts or errors, and/or elevating alerts or errors. In some embodiments when a subsystem detects an anomaly it may inform the SSS of the anomaly, and the SSS may categorize this information into one of a plurality of categories. In some embodiments the categories may be based on the cause and/or severity of the anomaly, and categories may include, but are not limited to, informational, performance, safety, and/or security.

In an exemplary embodiment informational anomalies may include, for example, single read failures, low battery power, or informational logs. When an informational anomaly is detected the SSS may send the anomaly information to a connected companion device or base station and/or may store the log information in the DSS. In some embodiments informational anomalies may be observed and tracked in order to identify trends.

In an exemplary embodiment performance anomalies may include, for example, storage failures or sensor read failures. When a performance failure is detected the SSS may update the appropriate bits in the status register for each performance anomaly and send or store that information in the DSS. In some embodiments, in response to a detected performance anomaly a major response error protocol may be instituted, and/or an over the air update may be sent.

In an exemplary embodiment safety anomalies may include, for example, rapid pressure changes, drug measurement failures, or CCS failures. When a safety anomaly is detected the SSS may send a separate emergency packet immediately, or the companion device may institute a security anomaly alert if the connection between the companion device and implant is compromised. In some embodiments, in response to a safety anomaly a critical error response protocol may be implemented, which may include, for example, re-implantation of the medical implant.

In an exemplary embodiment security anomalies may include, for example, invalid command authentications. When a security anomaly is detected the SSS may send a separate emergency packet immediately to the DSS for transmission. In some embodiments, in response to a security anomaly a security event response protocol may be implemented which may be, for example, monitoring.

In an exemplary embodiment the MPS may be responsible for, for example but not limited to, handling encryption and decryption of packets, serializing and deserializing packets into byte arrays for communication or storage, allocating data from each subsystem into packets, processing and validating commands and letting subsystems know of incoming commands, and/or determining if the firmware is in tracking or charging mode. In some embodiments the firmware may be built on a model that allows for the subsystems to respond and perform functions independently. The MPS may help coordinate the operator of each subsystem by handling communication between the subsystems.

In an exemplary embodiment the logic of one or more sub-systems may be abstracted to one or more timers. For example, a first timer may read sensors (such as, for example, pressure, temperature, volume, battery, and/or RSSI sensors), a second timer may create data packets to either be sent or stored, and a third timer may control a medication delivery mechanism such as the pump. It may be understood that in other embodiments more or fewer timers may be used, and the sub-systems may be distributed differently depending on the application.

In an exemplary embodiment the firmware may operate off an embedded system clock. In some embodiments a time synchronization method may be used in order to correct the system clock as it becomes out-of-sync with real world time.

An exemplary time synchronization method may involve the firmware receiving a baseline coordinated universal time (UTC) upon communicating with a patient-facing application. Periodically, as defined by a time sync interval, the companion device may post the current UTC, and the firmware may adopt the posted time and synchronize its internal counter to that time. The synchronization method may particularly be used in power down scenarios where a significant discrepancy may be introduced into the internal clock while powered off. It may be understood that in some embodiments all of the systems may be able to run on a timer accurate to the nearest second, rather than requiring sub-second accuracy. Therefore, periodic syncing of the method described above may be sufficient to maintain an accurate clock, and more power intensive methods of syncing may be avoided.

Figure 3:
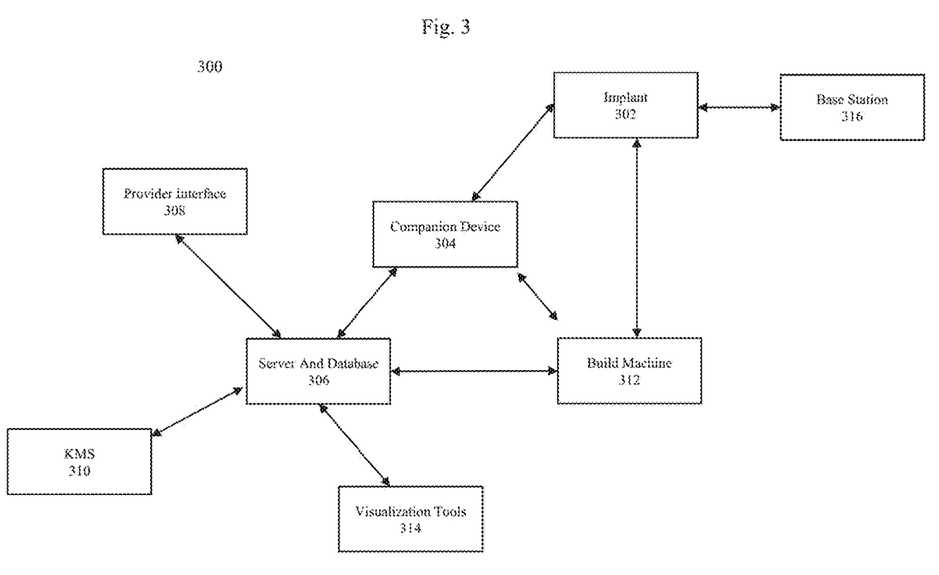
FIG. 3 is an exemplary illustration of interactions between the medical device and related firmware platforms.

In some embodiments one or more other software platforms may interact with the medical implant. Referring to FIG. 3 interactions between the medical device and exemplary related software platforms 300 may be shown. The software platforms 300 may include, but are not limited to, a medical implant 302, a companion device 304, a server and database 306, a provider interface 308, a key management system (KMS) 310, build machines 312, and/or visualization tools 314.

In some embodiments the medical implant 302 may send status packets, logs and/or emergency packets to the companion device 304 and may send constant tone extension (CTE) signals to the base station 316. In some embodiments the companion device 304 may send commands, time sync data, and/or DFU OTA's to the implant 302, and may send status packets, logs and/or emergency packets to the server and database 306. In some embodiments the server may send commands, DFU OTAs, and/or alerts to the companion device 304, encrypted commands to the provider interface 308, and/or implant-companion cryptographic keys, certificates, and/or private keys to the build machine 312.

In some embodiments the provider interface 308 may send commands to the server and database 306 and ultimately to the KMS 310. The commands sent to the KMS 310 may then be encrypted by the KMS 310. In some embodiments the KMS 310 may transfer cryptographic keys to the companion device either directly or via route of the server and database 306. The KMS 310 may act as a proxy to the server 306 for increased security. The KMS 310 may send encrypted commands to the provider interface 308 and may send cryptographic keys, certificates, and/or private keys to the build machine 312, both either directly or via route of the sever and database 306. The build machine 312 may send code and cryptographic keys to the implant 302, and code, certificates, and/or private keys to the companion device 304. The build machine 312 may further send companion device info and/or companion device assignment info to the server 306, and companion device and/or implant universal unique IDs (UUIDs) to the KMS 310 either directly or via route of the server and database.

In some embodiments a tracking mode may be used when, for example, the medical implant is attempting to establish a connection with an external system, such as the base station. While the advertising window is open, the firmware may send Constant Tone Extension (CTE) signals to the base station or other external system such as the base station. When the window closes, the CCS may notify the SCS through the MPS that a tracking mode has been entered, and may read the RSSI to establish a baseline RSSI value. After a pre-determined amount of time, for example 10 seconds, 15 seconds, a minute, etc, the SCS may read the RSSI again to determine the value has increased relative to the baseline RSSI value. If an increase is detected, the SCS may notify the MPS that charging mode has been entered. When the implant enters the charging mode the SCS may periodically read the RSSI to determine whether the implant is being charged. If RSSI decreases below a predetermined threshold, the implant may return to a default mode.

In one or more embodiments a patient-facing application may be included. The patient-facing application may be installed on, for example, the companion device, and may, for example, serve as a router that connects the medical implant to a server, act as a processor that processes and interprets implant data, and/or act as a patient interface for the patient to interact with the medical implant. The companion device may be enrolled with a device management application that may restrict network connectivity, device functionality, and/or device settings for security or compatibility reasons. For example, in an exemplary embodiment only basic accessibility preferences such as text size, brightness, etc may be freely modified from the companion device. In an exemplary embodiment network connectivity may be limited to communication with allowed resources, such as the medical implant and related resources, resources related to application or device functionality, etc, and Bluetooth and/or internet connectivity setting may be set to always be enabled.

The patient-facing application may have a plurality of functionalities, including but not limited to, facilitating communication between the implant and the server, processing data received from the implant and the server, storing data received from the implant and the server if a connection is disrupted or otherwise unavailable, and/or displaying information to a user or patient. The patient-facing application may include a plurality of architectural components including, for example, a notification service, a client service, an implant connection management service, a key service, a data processing service, a data reliability service, and/or a plurality of UI components.

In an exemplary embodiment, updates to the patient-facing application may be applied using a mobile device management application. While an update is being applied it may be understood that the application may be unable to receive information from or send information to the implant. In order to mitigate these issues, the implant's reliability functionality may ensure that packet loss is minimized or eliminated, and further any commands sent to the companion device may result in a response sent to the server to confirm that the command was received. If the response is not received by the server, for example due to the updating process, a recovery response may be initiated.

In an exemplary embodiment, the base station may power the implant through object tracking and antenna steering. The base station may have a plurality of operating states, for example there may be a default mode, a tracking mode, and/or a charging mode. The default mode may be used when the medical implant is being used in normal operation, and the AoA service may be set at the default advertising window. The implant may start in a default mode and may advertise to the base station to seek a connection at set intervals. The advertising window for the base station may be separate and unrelated from the advertising window for the companion device. When a connection between the implant and the base station is established the implant may enter a tracking mode, which may involve, for example, sending CTE or another signal type which can be received by a base station antenna array to determine relative position. In some embodiments the base station firmware may isolate the connectivity, tracking, and beam-steering components of the system.

In an exemplary embodiment historical data on devices and logs may be stored in a database. The database may additionally help maintain the state of commands for ongoing systems. In an exemplary embodiment a server may provide a standard way to adjust database information and may act as a network bridge or an API retrieval source for other software platforms, for example the patient-facing application, provider interface, and/or dashboards or other visualization tools. In some embodiments the server and database may communicate on a shared virtual private cloud, which may allow for local network connection. The database may not be publicly accessible and may only accept access from the server or server's IP address. The database may have two accounts, a root account, and an account with read/write to table permissions, which may operate the corresponding server instance.

In some embodiments the server may utilize inputs to perform operations, the inputs may include, but are not limited to, path parameters, request headers/data, and/or query parameters. The operations that utilize the inputs may include, but are not limited to, read operations, write operations, and update operations to the database. Database operations within an endpoint may be bundled in transactions, which may ensure that the transaction is an atomic operation. Endpoints may return a response, including for example a response code and/or potential data.

In an exemplary embodiment the provider interface may allow healthcare providers to adjust characteristics of the medical implant without requiring physical access to the device. The provider interface may be provided on a provider device, which may be, for example, a computer, tablet, iPad, etc. In some embodiments this may allow the implant to be compatible with telehealth environments and may assist in protecting the medical implant against physical attacks from, for example, magnets or wands. Furthermore, the implanted device may no longer need to be within a short distance of the controlling system.

The provider interface may be composed of several sub-units, including but not limited to authentication, associated patients, command issuing, and/or real time command statuses. In an exemplary embodiment command issuers may be restricted to specific patient devices, as determined by a central patient index. The index may be stored in the server's database and may only be alterable by specific authorized systems. The central patient index may be updated internally during, for example, the distribution of a device to a patient and provider. In some embodiments there may be a two-layer authentication system. The first layer may be, for example, a device level authentication system, where biometrics, pins, and/or passwords may be required to access the device. The second layer may be, for example, a VPN security layer, where in order to access the required VPN a multi factor authentication system will need to be used. Additionally, the provider may need to periodically reauthenticate when using the device, for example authenticating after login, and also before any command is sent, and/or periodically based on time, e.g. every 5 or 10 minutes.

In an exemplary embodiment command issuers may view and select their patients from the provider interface. Restrictions on the server side may be applied so that command issuers are limited to viewing only their patients. The provider may be able to view all of their patients through a display, and based on permission may be able to see further information on specific patients, for example but not limited to, patient name, contact information, address, and/or picture. Patient related alerts or requests for contact may be available on one or both of the general patient display or the specific patient display.

In an exemplary embodiment the provider interface may format commands to send to the server, encrypt commands with the KMS, transmit commands to the server, and/or update UI elements when a command status is updated. The provider interface may also issue real-time command statuses, as after sending a command, the command issuer may need to know that the command was successfully executed.

In an exemplary embodiment the KMS may perform key lifecycle management, which may include the creation, destruction, storage, and/or distribution of cryptographic material in order to support cybersecurity of the medical implant and related systems. The KMS may be implemented on multiple different systems. The KMS may be divided into two parts, one part may exist in a physical device, such as a physical hardware security module (HSM), while a second parts exists in a virtual space such as Amazon Web Services or similar cloud environments. Less sensitive material, for example the parts of the KMS that handle cryptographic keys, or the compute logic servicing, may be hosted in the virtual environment. More sensitive material, for example root certification signing keys, may exist in the HSM.

In an exemplary embodiment one or more build machines may administer the initial deployment and subsequent updating of the medical implant device and companion devices. The build machines may be a physical device located in a secure location and may interface with the physical and/or virtual aspects of the KMS to manage certificates. In some embodiments the build machines may handle the initial flashing, preparation, and configuration of the medical implant boards before installation of the boards. The build machines may also communicate the creation of the boards and their configurations to the server and may pair the medical implant with a companion device, for example by creating a QR code for the companion device to use to retrieve the appropriate keys for communicating with a specific medical implant board.

The build machines may also handle DFU processes. The build machines may build the DFU package, get the package signed by a DFU key, encrypt and store the packages, and/or inform the server to notify the companion device to retrieve the package to begin updating the medical implant.

In some embodiments there may be one or more separate companion device build machines for the companion device. The companion build machines may perform the initial configuration of the companion device so the companion device may have the necessary configuration profiles and mobile device management systems installed. The companion build machines may interface with a certificate administration interface to create certificates for the companion device. The initial companion device provisioning process may require physical access to the companion device. The companion build machines may also build application packages and updates for the companion device.

In an exemplary embodiment one or more visualization tools may be used to visualize information about the medical implant. Visualization tools may include, for example, a data dashboard, a fleet management system, a server API client, etc. The visualization tools may include information on, including but not limited to, alerts, summary statistics, medical implant PCBs, medical implant or related systems tests, diagnostics and statues, status and/or statuses of commands or updates. These tools may access the server in order to obtain information, and may be used by, for example, engineers or developers in order to obtain general information on the medical implant system operations. In some embodiments the data may include averages, means, statistical trends, standard deviations, or other aggregations of a plurality of medical devices, or data related to a specific device's current state or earlier states.

In some embodiments, these tools may include a GUI or other display which may visually show the data. Some examples of data that may be recorded or shown include, medical device fluid levels, battery charge or lifetime, medical implant fluid pressure, medical implant fluid type, medical implant implantation location, disease response, etc.

In an exemplary embodiment communication between the companion device and the server may be facilitated using, for example, push notifications and/or HTTP requests. The patient-facing application may receive commands, keys, and other information via, for example, push notifications. These notifications may be processed and acted on using, for example, a notification service, which may parse the notifications payload and perform the appropriate action via the corresponding function. The patient-facing application may support multiple categories of push notifications, such as callback requests where the server sends a URL from which the patient-facing application can request additional data from the server or alerts which may trigger pop-ups, alarms, sounds, or other notifications of the companion device. Callback requests may come in a variety of forms, and may include payloads on the assigned patient, the board assignment, on commands, on the device firmware update (DFU), or on storage erasure. In some embodiments the patient-facing application may send and receive data through a client service.

A notification with an assigned patient payload may trigger a function that uses a Key Service, responsible for handling any interactions with a secure storage system, such as securely storing new patient information. Passing an invalid action may result in no action being taken, and a security event may be noted and reported to the server. A notification with a board assignment payload may trigger a function that uses the Key Service to save a new key and board information to secure storage. A notification with a command payload may trigger a function to store a command for later transmission to the implant, or to execute a command on the companion device.

A notification with a DFU payload may trigger a function that stores the downloaded encrypted DFU firmware executable to the application's secure file system and notifies the user on the UI that a DFU update is pending. A notification with an erase storage payload may trigger a function to erase everything in some or all forms of persistent storage—for example any persistent secure or unsecure storage, and/or the file system.

In an exemplary embodiment communication between the medical implant and the companion device may be facilitated through an implant connection management service (ICMS). In an embodiment, the ICMS may periodically listen for advertising from the implant in order to connect to the implant. The ICMS for a particular patient-facing application may be restricted to only looking for advertisements from one or a specific subset of implants to which it is assigned. The initial assignment may be, for example, during a registration process or through push notifications.

In some embodiments the patient-facing application may route OTA DFU's or commands sent by the server or another interface to the medical implant. When a connection with the medical implant is made, the patient-facing application may check local storage for pending commands, validate the command's expiration date, reject and/or inform the server of expired commands, and/or encrypt the command with a cryptographic key and transmit the command over the data/command characteristics. In some embodiments for over the air DFU's a DFU firmware executable may be received from the server, which the patient-facing application may store in local storage. When a connection with the medical implant is made, the patient-facing application may retrieve the OTA DFU, decrypt it with a private key, validate the update expirations date, and/or send the firmware executable over the implant's DFU characteristic. In some embodiments the patient-facing application may notify the user and/or server of the result of the update.

In an embodiment the implant may send packets and logs to the companion device, which the patient-facing application may route to the server. Packets may first be decrypted and parsed before being sent. In some embodiments, if a parsing failure is detected, the data may still be sent as decrypted but unparsed, and a notification that the data is unparsed may be included.

In some embodiments parsing and interpretation of data sent by the implant may be limited to the patient-facing application, which may minimize logic duplication. The server application logic may be restricted to, for example, simple operations like unit conversion, and the companion device may handle all other processing such as converting raw values to readable values, determining alerts, etc. If the patient-facing application's logic determines that an alert should be raised, it may trigger a UI alert notifying the user, and/or may pass the parsed data up to the server with information about the alerts triggered. The server may then act in accordance with the patient-facing application's determination of the alert.

In some embodiments if the parsing or decryption on the patient-facing application fails, the patient-facing application may send the unparsed or unencrypted data to the server, along with an indication of the failure to parse or encrypt as an error. The user may also be notified of the failure via the patient-facing application or other UI elements.

In some embodiments operation of the implanted medical device may involve functionality that occurs across multiple software platforms, for example via the transmission of status packets. The interaction between these multiple platforms may be understood as data flows, which may include, but are not limited to, the sending and receiving of status packets, commands, implant errors, DFU OTAs, cryptographic material for implant—patient-facing application communication, certificate update and replacement, over the air update of the patient-facing application, flashing, and/or defining device and manufacturing information. It may be understood that in some embodiments certain platforms may be restricted to sending or receiving data flows to specific other platforms.

In an exemplary embodiment status packets and logs may originate in the implant, and may include, for example but not limited to, pump data, sensor readings, status data, and/or indication of time accuracy. The status packets may then travel to the companion device and may be decrypted and parsed. The patient-facing application may use the status and most-recent sensor data to display data to the patient. The rest of the data may be sent to the server to be parsed and stored in separate models for each data entry. The data may be analyzed by dashboards or other visualization tools.

In an exemplary embodiment commands may originate from a physician or other authorized person, who may, for example, enter the command information through a GUI. The command may then be formatted and encrypted, for example with an ephemeral symmetric key through KMS. The provider interface may then be sent the encrypted command and an encrypted ephemeral key. The encrypted command and key may then then be sent to the server, the server may verify or acknowledge receipt, for example by sending the provider interface a code. The command may be stored in the database and may have a corresponding status, for example "server_received" or "queued_for_transmission". The server may then communicate to the companion device that a new command was issued. The request may then be approved by the patient or user through the patient-facing application, in some embodiments the clinician or healthcare provider may also be required to approve the request, for example by inputting a unique numerical code. Once the requisite approvals have been given the command may be decrypted and stored in the patient-facing application's local filesystem. The next time a connection between the companion device and the implant is established, the command may be transmitted to the implant, decrypted by the implant, and instituted.

In an exemplary embodiment, when an error occurs on the implant, the error may be captured in the status, or as a log. The status and/or log may be sent to the patient-facing application and displayed as necessary and forwarded to the server for processing. In some embodiments the errors may trigger one or more alert systems, in accordance with an error response protocol for the relevant error class.

In some embodiments the companion device may be configured to give visual or auditory alerts based on transmitted medical implant data. There may be a plurality of predetermined or adjustable thresholds for the medical implant based on a variety of factors, for example low battery state, low medication in the medical implant, patient abnormalities detected by the medical implant sensors, etc. In some embodiments alerts may be tied to a determination that the medical implant has been compromised. Determinations that the implant has been compromised may include, for example, detection of failed OTA cryptographic verification, failed command cryptographic verification, commands that pass verification but are repeats of previously used commands (i.e. the ID number of the command is an already used ID number), there is a mismatched firmware signature, and/or there are decryption issues that might indicate the cryptographic key has been compromised. In some embodiments alerts may be tied to a determination that the patient app has been compromised. Determination that the patient app has been compromised may include, for example, detecting failures in the app allowing someone to access the app code and forge data and/or failure for the app to pass a signature check on boot up. In some embodiments the auditory or visual alerts may be given if the companion device is not connected to the internet, and the alerts may include beeps, buzzing, flashing lights, push notifications, etc. In some embodiments the alerts may be given continuously or periodically until acknowledged by the user. The relevant data may also be held by the companion device until a connection with the internet is reestablished, which may happen automatically at the time an internet connection is established. After the connection is reestablished, the companion device may attempt to periodically fetch data from the server.

Once the companion device connection to the server is re-established, the server may then forward the alerts and related data to healthcare providers or other relevant personnel.

The bonding process of the companion device may now be discussed in more detail.

In an exemplary embodiment the companion device may be prepared using a build machine as discussed above, during this process the patient-facing application may be installed on the companion device as part of an application bundle. Included in the application bundle may be a general companion device certificate, which may be restricted to be used only during initial registration of the application to establish a connection with the server and to download the companion device's specific certification.

After the patient-facing application is installed on the companion device, when the application opens for the first time, a registration process may begin. The user may be prompted to scan a QR code or other barcode in order to register the companion device. The server may generate a QR code to be used for the companion device to register with the server, which may be triggered by the flashing procedure initiated by the build machine. Once the QR code is scanned, the companion device may use its general certificate to communicate device-specific registration information, which may include its configuration, the name of the device, and/or its serial number to the server using the one-time username, password, and/or URL contained in the QR code. Utilizing this information, the server may send a push notification to the companion device with a URL from which the patient-facing application can retrieve its device-specific certificate to be stored in the companion device's secure hardware for key storage, to use for all future communications with the server.

In an exemplary embodiment, once the companion device has been successfully registered a medical device assignment process may begin. The patient-facing application may indicate a successful registration and may prompt the user to scan a QR code to associate the companion device with an implant. The QR code may contain, for example, a one-time single-use link to obtain the implant's cryptographic key and any other implant device system specific information, such as for example, battery configuration, implant name, implant settings, etc. The code may be generated by the server and the implant build machine when the implant is flashed. The patient-facing application may then obtain a URL which may be used to obtain the above information, which may be stored in the secure storage and/or the implant file system. When the assignment process is completed, the implant and companion device may be registered with the server.

After a successful assignment, the patient-facing application may prompt the user to pair the companion device with the implant. The companion device may need to be within a certain proximity to the implant to be paired, for example within the range of the Bluetooth signal emitted by the implant. When pairing is initiated on the companion device the companion device may continually search for an advertised signal by the specified implant. When the implant is discovered the implant may respond to the companion device signal, for example with an encrypted version of the implant's default bonding code, which may be modified with, for example, an index. The patient-facing application may then decrypt the responding message and send an encrypted version of the code with an incremented index. Once the validation of the code and index is completed, the implant may initiate a bonding handshake, and the user may be prompted to enter a passcode on the companion device. If the passcode is correctly entered the bonding may be completed and continuous or periodic communication between the implant and the companion device may be facilitated.

Figure 4:
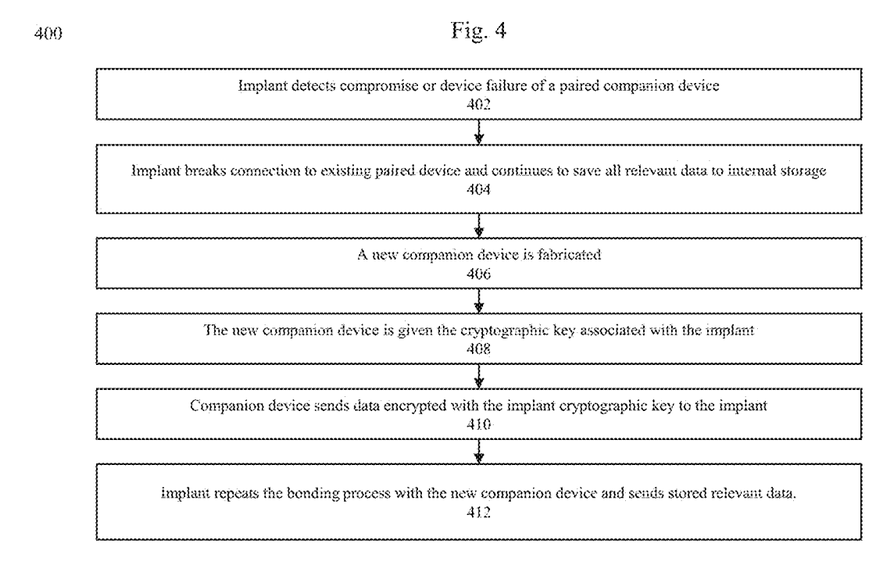
FIG. 4 is an exemplary method for restoring a broken or compromised companion device to a medical implant.

Referring to FIG. 4, an exemplary method for restoring a broken or compromised companion device to a medical implant 400 may be shown. In a first step 402 the medical implant may detect that a connected companion device has been compromised or that there was a device failure, for example by determining that the companion device has not connected in a predetermined period of time, based on an alert given by the patient, and/or based on installed diagnostic tools or intrusion detection systems that might, for example, monitor inbound traffic. In a next step 404 the implant may break its connection to the existing paired device and continue saving all relevant data to the implant's internal storage. In a next step 406 a new companion device may be fabricated. In a next step 408 the new companion device may be given the cryptographic key associated with the implant, from, for example, the companion build machine. The cryptographic key associated with the implant may be obtained by the companion build machine from, for example, the KMS. In a next step 410 the companion device may send data encrypted with a pre-shared key to the implant. In a next step 412 the implant may repeat the bonding process described above with the new companion device, and may send all relevant data stored during the duration where no companion device was connected to the new companion device.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for remotely bonding a companion device to an implanted medical device, comprising:
   periodically determining if the companion device is bonded to the implanted medical device;
   when no device is bonded to the implanted medical device, advertising a periodic signal containing an encrypted number from the implanted medical device, wherein the encrypted number is encrypted by a cryptographic key associated with the implanted medical device;
   receiving, by the companion device, the periodic bonding signal from the implanted medical device;
   decrypting, by the companion device, the encrypted number transmitted by the periodic bonding signal data using the cryptographic key information, resulting in a decrypted number; creating, by the companion device, a response to the decrypted number; encrypting, by the companion device, the response to the decrypted number;
   transmitting the encrypted response to the decrypted number to the implanted medical device;
   validating, by the implanted medical device, the transmitted response;
   triggering the implanted medical device to accept and establishing new bonded connections between the companion device and the implanted medical device; and
   monitoring and/or diagnosing a patient's health conditions with the implanted medical device by:
   detecting a cause for concern;
   sending, to the companion device through the bonded connection, an alert about the cause for concern;
   wherein the cause for concern is that the implanted medical device has been compromised;
   wherein the implanted medical device is configured to automatically break the connection to the companion device and continue to save all relevant data to internal storage when the implanted medical device has been compromised; and
   wherein the cryptographic key information associated with the implanted medical device is provided to the companion device by a build machine at the time the companion device is manufactured.

2. The method of remotely bonding of claim 1, wherein the bonded connection between the companion device and the implanted medical device is a direct short-range wireless connection.

3. The method of remotely bonding of claim 2, wherein the implanted medical device is a craniofacial implant and the companion device is a tablet.

4. The method of remotely bonding of claim 1, wherein the implanted medical device is physically inaccessible.

5. The method of remotely bonding of claim 1, wherein the implanted medical device is one of a spine implant or an orthopedic joint implant and the companion device is a tablet.

6. A system for remotely bonding a companion device to an implanted medical device, comprising;
   the implanted medical device periodically determines if the companion device is bonded to the implanted medical device, wherein if no device is bonded to the implanted medical the implanted medical device periodically advertises a signal containing an encrypted number that is encrypted by a cryptographic key associated with the implanted medical device;
   a companion device which is provided with the cryptographic key associated with the implanted medical device and which receives the periodic bonding signal from the implanted medical device, determines a decrypted number by decrypting the encrypted number using the cryptographic key information, creates a response to the decrypted number, encrypts the response to the decrypted number, and transmits the encrypted response to the decrypted number to the implanted medical device;
   wherein the implanted medical device validates the transmitted response and establishes a bonded connection between the companion device and the implanted medical device;
   wherein the implanted medical device monitors and/or diagnoses a patient's health conditions and detects causes for concerns,
   wherein the cause for concern is that the implanted medical device has been compromised;
   sending, to the companion device through the bonded connection, an alert about the cause for concern; and
   wherein the implanted medical device is configured to automatically break the connection to the companion device and continue to save all relevant data to internal storage when the implanted medical device has been compromised; and
   a build machine that provides the cryptographic key information associated with the implanted medical device to the companion device at the time the companion device is manufactured.

7. The system for remotely bonding of claim 6, wherein the bonded connection between the companion device and the implanted medical device is a direct short-range wireless connection.

8. The system for remotely bonding of claim 7, wherein the implanted medical device is a craniofacial implant and the companion device is a tablet.

9. The system for remotely bonding of claim 6, wherein the implanted medical device is physically inaccessible.

10. The system for remotely bonding of claim 6, wherein the implanted medical device is one of a spine implant or an orthopedic joint implant and the companion device is a tablet.

\* \* \* \* \*